United States Patent [19]

Watanabe et al.

[11] Patent Number: 5,093,200
[45] Date of Patent: Mar. 3, 1992

[54] MULTILAYER SUSTAINED RELEASE GRANULE

[75] Inventors: Sumio Watanabe, Aichi; Ichiro Yamakawa, Ibaraki; Hidenobu Ando; Nobutaka Noda, both of Kagamigahara; Yasuo Miyake, Inuyama, all of Japan

[73] Assignee: Eisai Co., Ltd., Tokyo, Japan

[21] Appl. No.: 253,367

[22] Filed: Sep. 30, 1988

Related U.S. Application Data

[63] Continuation of Ser. No. 919,902, Oct. 16, 1986, abandoned.

[30] Foreign Application Priority Data

Oct. 23, 1985 [JP] Japan ................ 60-235412

[51] Int. Cl.$^5$ .................. B32B 27/00; A61K 9/56
[52] U.S. Cl. .................. 428/407; 424/468; 424/472; 424/476; 424/494; 424/498; 428/402.2; 428/402.21; 428/402.24; 428/403
[58] Field of Search ........... 428/402.2, 402.21, 402.22, 428/402.24, 403, 407, 497, 532; 604/890; 424/468, 472, 476, 494, 498, 490

[56] References Cited

U.S. PATENT DOCUMENTS

| | | | |
|---|---|---|---|
| 3,577,512 | 10/1968 | Shephard et al. | 424/19 |
| 4,122,157 | 10/1978 | Huber | 424/492 |
| 4,155,993 | 5/1979 | Belleville et al. | 424/19 |
| 4,261,970 | 4/1981 | Ogawa et al. | 424/19 |
| 4,309,405 | 1/1982 | Guley et al. | 424/493 |
| 4,309,406 | 1/1982 | Guley et al. | 424/489 |
| 4,341,563 | 7/1982 | Kurihara et al. | 106/171 |
| 4,404,183 | 9/1983 | Kawata et al. | 424/19 |
| 4,454,108 | 6/1984 | Iida et al. | 424/19 |
| 4,483,846 | 11/1984 | Koide et al. | 424/19 |
| 4,552,751 | 11/1985 | Inaba et al. | 424/19 |
| 4,568,536 | 2/1986 | Kronentahl et al. | 424/19 |
| 4,572,833 | 2/1986 | Pedersen et al. | 424/38 |
| 4,600,645 | 7/1986 | Ghebre-Sellassle et al. | 424/19 |
| 4,609,542 | 9/1986 | Panoz et al. | 424/38 |
| 4,708,874 | 11/1987 | Dehaad et al. | 424/470 |
| 4,713,248 | 12/1987 | Kjornaes et al. | 424/468 |
| 4,716,041 | 12/1987 | Kjornaes et al. | 424/468 |
| 4,844,905 | 7/1989 | Ichikawa et al. | 424/451 |

FOREIGN PATENT DOCUMENTS 2721603  5/1976  Fed. Rep. of Germany ...... 428/407

OTHER PUBLICATIONS

"Stearate" Definition: Hackh's Chemical Dictionary-4th ed., Ed.; Julius Grant.

*Primary Examiner*—George F. Lesmes
*Assistant Examiner*—Christopher Brown
*Attorney, Agent, or Firm*—Flynn, Thiel, Boutell & Tanis

[57] ABSTRACT

A multilayer granule of the invention comprises a core, a slow-release layer, a rapid-release layer to be provided outer of said slow-release layer and a film layer containing a metal stearate and being deposited between the slow-release layer and the rapid-release layer. A pharmacologically effective component is kept to discharge for long.

13 Claims, No Drawings

MULTILAYER SUSTAINED RELEASE GRANULE

This application is a continuation of U.S. Ser. No. 919,902, filed Oct. 16, 1986, now abandoned.

This invention relates to a multilayer granule comprising a rapid-release layer formed around a slow-release phase. Namely, a moiety capable of slowly releasing ingredients and another moiety capable of rapidly releasing the same are integrated in the granule of the present invention, which makes it possible to sustain the release of said ingredients for a prolonged period of time. Some pharmaceuticals require such sustained release. Thus the present invention is available in the field of pharmaceuticals.

STATEMENT OF PRIOR ARTS

It is often required in pharmaceuticals to depress the concentration of a medicine in vivo as low as possible and to sustain the same for a desired period of time. There have been attempts to produce sustained release preparations of various formulations which are destined to achieve the above object. These formulations include a medicine wherein a rapid-release moiety and a slow-release moiety are separately formed and integrated for administration. Particular examples thereof are a so-called double-layer tablet produced by coating a slow-release core with a rapid-release layer and molding the whole as a single tablet; a hard capsule produced by separately preparing slow-release granules and rapid-release granules and enclosing a mixture of the same into a capsule; and a tablet produced by compressing the above-mentioned granules together with excipients. In these preparations, the release of ingredients is performed in vivo repeatedly with a proper time lag. Thus the concentration of the ingredients in vivo is maintained constant for a prolonged period of time on the whole.

It is expected that sustained release preparations of the type other than those described above can be devised. A so-called multilayer granule is one of these expected formulations.

The process for integrating slow-release granules and rapid-release granules by mixing them has a disadvantage that the compositional ratio of the two components can not be constant but varies widely. It is believed that this disadvantage is brought about by the great difficulty in the mixing procedure in addition to stochastic variance. Such a wide variation in the compositional ratio significantly lowers the reliability as well as usefulness of the sustained release preparation. In contrast thereto, multilayer granules show a small variation in the compositional ratio in the administration since they consist of single granules containing a slow-release moiety and a rapid-release moiety in a given ratio. Accordingly a multilayer granule is expected as an excellent sustained release formulation.

However the multilayer granule has a serious disadvantage that the release-controlling mechanism of the slow-release moiety is damaged during the formation of the rapid-release moiety thereon. Although the reason thereof has not yet been sufficiently clarified, it may be supposed that a solvent required for the formation of the rapid-release moiety might moisten the slow-release moiety or that an external force required for the formation of the rapid-release moiety might be transmitted to the slow-release moiety to thereby damage a delicate release-controlling mechanism of the latter. Anyhow the destruction of the release-controlling mechanism results in the loss of the slow-release effect and thus the slow-release moiety is released at the same time with the rapid-release moiety, as will be shown in the Experimental Examples hereinbelow.

In order to overcome this disadvantage, we have attempted to form a blocking film layer at the boundary between the slow-release moiety and the rapid-release moiety to protect the release-controlling mechanism of the former therewith. Thus we have examined various film-forming materials whether they are available for this purpose or not. However no conventional film can give the desired result as will be shown in the Experimental Example hereinbelow. Thus it has become the object of an invention to provide a film layer composition capable of achieving the above-mentioned purpose.

SUMMARY OF THE INVENTION

Under these circumstances, we have performed various examinations and have consequently found that a film layer containing a metal stearate can protect the release-controlling mechanism of the slow-release moiety against destruction and allow said moiety to fully exhibit the desired function, to thereby complete the present invention.

Accordingly, it is an object of the present invention to protect the release-controlling mechanism of a slow-release moiety of a multilayer granule consisting of said slow-release moiety and a rapid-release moiety. In order to achieve this object, the present invention discloses a technique where a layer containing a metal stearate as an essential ingredient is provided at the boundary between said slow-release moiety and said rapid-release moiety.

A multilayer granule of the invention comprises a core, a slow-release layer, a rapid-release layer to be provided outer of said slow-release layer and a film layer containing a metal stearate and being deposited between the slow-release layer and the rapid-release layer. A pharmacologically effective component can be discharged at a controlled rate for long periods of time.

Now the present invention will be described in detail.

The term "multilayer granule" is used herein as a concept corresponding to a so-called multilayer tablet. By the multilayer tablet is generally meant one wherein a tablet core is coated with concentric layers different from each other in the properties or composition. In particular, a double-layer tablet is called a cored tablet. It is noted that the multilayer structure denotes one wherein concentric layers, differing from each other in properties or compositions, are laminated and integrated. The same meaning is used in the present invention. Thus, by the multilayer granule is meant a granule wherein a number of layers different from each other in the properties or composition are laminated and integrated. The core of the granule is particularly called a nuclear particle. A nuclear particle which is merely a seed for producing granules is called a nuclear seed.

In the present invention, a number of layers, differing from each other, in the properties or compositions particularly comprise a slow-release moiety and a rapid-release moiety. Thus the present invention is restricted to a multilayer granule wherein a rapid-release layer is formed around a slow-release phase. The terms "slow" and "rapid" as used herein are relatively determined. That is to say, when there are two moieties showing different release initiation times from each other, the one having a later release initiation time is called "slow-release" while the other is called "rapid-release". Therefore in the case of a structure where an internal layer is enclosed in an intermediate layer which, in turn, is enclosed in an external layer, the internal layer is slow-release in contrast to the intermediate one which is thus rapid-release, while the same intermediate layer is, in turn, slow-release in contrast to the external one which is thus rapid-release.

According to this definition, the rapid-release moiety invariably serves as an enclosing layer. Thus it will be merely called the rapid-release layer in the present invention.

On the other hand, the slow-release moiety usually serves as an enclosing layer, but it sometimes plays the role of a nuclear particle per se. Thus it will be generally called a slow-release phase hereinbelow. Thus the term "slow-release phase" includes both a slow-release enclosing layer and a slow-release nuclear particle.

Since the slow-release phase and the rapid-release layer are discrete, there exists a clear-cut boundary between them. The present invention is characterized in that a film layer containing a metal stearate as an essential ingredient is present at this boundary. A film layer means a layer which comprises a film-forming material and is made into film thereby. Examples of the film-forming material are ethylcellulose, hydroxypropylmethylcellulose, shellac and wax.

Examples of usually available metal stearates are calcium stearate and magnesium stearate. These compounds are available in the present invention. A preferable content of the metal stearate in the film layer may vary depending on other ingredients therein such as talc or wax. It is generally employed in an amount of 10 to 80%, preferably 15 to 70%. However the present invention is not restricted by the above range. Thus the amount of the metal stearate in the film layer may be arbitrarily determined depending on the composition of the film layer. The film layer may be formed in a conventional manner. For example, a film-forming material, a metal stearate and other ingredients were dispersed in ethyl alcohol to thereby form a film layer solution. Then the granules to be coated therewith are made to flow on a fluid bed or to rotate in a tumbling granulator while spraying the above-mentioned film layer solution thereon.

The multilayer granule of the present invention may be produced in the following manner. First a slow-release nuclear particle or a granule seed is prepared. A generally available granule seed comprising a mixture of white sugar and corn starch, which will be abbreviated as an NPS hereinafter, may be employed. The nuclear particle may be prepared by kneading a pharmaceutical ingredient to be slowly released with other ingredients such as wax with the use of a binder and extruding the mixture to form a pellet. However the present invention is not restricted by the particular production of the nuclear particle or seed. A slow-release enclosing layer may be formed around the nuclear seed in a conventional manner.

Then the particle coated with a slow-release enclosing layer or a nuclear particle containing pharmaceutical ingredients is coated with a film layer which contains a metal stearate as an essential ingredient. The coating may be performed in the above-mentioned manner, i.e., by making the particle to flow or to tumble while spraying the film layer solution thereon.

The intermediate particle thus obtained may be further coated with a rapid-release layer in the following manner. First ingredients of the rapid-release moiety are dissolved and dispersed in water to give a rapid-release layer solution. Then the intermediate particle is made to flow or to tumble while gradually adding the rapid-release layer solution thereto to thereby laminate the latter on the former followed by air-drying.

The particle thus obtained may be further coated with another rapid-release layer by repeating the procedures for applying the film layer and the rapid-release layer. Thus a multilayer granule consisting of three or more layers may be produced.

The multilayer granule thus obtained may be administered as a medicine as such. Alternately it may be formulated into a capsule by enclosing the same in a hard capsule or into a compressed tablet by mixing with other ingredients and compressing the mixture. These preparations comprising the multilayer granule may be prepared by a method conventionally known in the art. Thus no special attention is required.

FUNCTION

It is a function of the present invention to sustain the release of medicinal compounds in a multilayer granule, which have been considered difficult in conventional multilayer granules. The reason for this difficulty is that laminating a number of layers in a multilayer granule would physically and chemically damage the release-controlling mechanism of a slow-release moiety. The present invention has solved this problem and has made it possible to sustain the release of a medicinal compound in a multilayer granule. In particular, it provides a multilayer granule highly resistant against filling and compression forces. Thus the release of a medicinal compound can be sustained even if the multilayer granule is enclosed in a hard capsule or formulated into a compressed tablet. In addition, this function of the present invention can be consistently maintained even under various storage conditions.

EXAMPLES

To further illustrate the present invention, the following Examples will be given.

EXAMPLE 1

1.4 kg of 28- to 32-mesh white sugar-corn starch granules (NPS) was employed as nuclear seeds. The seeds were tumbled in a small plate tumbling granulator and a solution prepared by dissolving and dispersing 400 g of dextromethorphan hydrobromide, 20 g of ethylcellulose, 20 g of purified shellac and 160 g of microcrystalline wax in 1.9 kg of ethyl alcohol was slowly added thereto to thereby laminate the latter on the former. Then the particles were air-dried at 50° C. for 12 hours. The particles thus obtained and the layer thus laminated thereon were referred to as R particles and R layer respectively.

1.5 kg of the R particles were tumbled in a small plate tumbling granulator and a solution prepared by dispersing 300 g of calcium stearate, 15 g of ethyl cellulose and 15 g of purified shellac in 2.2 kg of ethyl alcohol was gradually added thereto to thereby laminate the latter on the former. Then the particles were air-dried at 40° C. for 12 hours. The particles thus obtained and the layer thus laminated thereon were referred to as C particles and C layer, respectively.

1.22 kg of the C particles were tumbled in a small plate tumbling granulator and a solution prepared by dissolving and dispersing 100 g of dextromethorphan hydrobromide, 1 kg of diprophylline, 140 g of light silica, 140 g of talc and 20 g of corn starch in 3.2 kg of ethyl alcohol was gradually added thereto to thereby laminate the latter on the former. Then the particles were air-dried at 40° C. for 12 hours. The particles thus obtained and the layer thus laminated thereon were referred to as I particles and I layer, respectively. The I particles were prepared as the multilayer granules of the present invention.

For reference, the overall weight ratio of the ingredients of the nuclear seed and each layer will be shown:

| | | |
|---|---|---|
| nuclear seed | NPS | 70; |
| R layer | dextromethorphan hydrobromide | 20; |
| | ethylcellulose | 1; |
| | purified shellac | 1; |
| | microcrystalline wax | 8; |
| C layer | calcium stearate | 20; |
| | ethylcellulose | 1; |
| | purified shellac | 1; |
| I layer | dextromethorphan hydrobromide | 10; |
| | diprophylline | 100; |
| | light silica | 14; |
| | talc | 14; and |
| | corn starch | 2. |

EXAMPLE 2

The procedure of Example 1 was followed except that the amount of the NPS in the formulation was not 70 but 60 and that the C layer had the following three compositions to thereby give three types of multilayer granules (1), (2) and (3), each prepared as the multilayer granules of the present invention:

| | (1) | (2) | (3) |
|---|---|---|---|
| C layer: magnesium stearate | 25 | 22.5 | 20; |
| vinyl acetate | 2 | 2 | 2; and |
| methylcellulose | 2.5 | 5 | 7.5. |

EXAMPLE 3

The procedure of Example 1 was followed except that the C and I layers had the following compositions to thereby give four types of multilayer granules (4), (5), (6) and (7), each prepared as the multilayer granules of the present invention:

| | (4) | (5) | (6) | (7) |
|---|---|---|---|---|
| C layer calcium stearate | 20 | 15 | 10 | 5; |
| talc | 5 | 10 | 15 | 20; |
| ethylcellulose | 1 | 1 | 1 | 1; |
| purified shellac | 1 | 1 | 1 | 1; |
| I layer dextromethorphan.hydrobromide | | | | 10; |
| diprophylline | | | | 100; |
| light silica | | | | 5; |
| talc | | | | 10; |
| corn starch | | | | 5; and |
| polyethylene glycol | | | | 5. |

Every granule had the same I layer.

EXAMPLE 4

The procedure of Example 1 was followed to give multilayer granules of the following formulation which were prepared as the multilayer granules of the present invention:

| | | |
|---|---|---|
| nuclear seed | NPS | 80; |
| R layer | dextromethorphan hydrobromide | 20; |
| | octyl decyl triglyceride | 5; |
| C layer | calcium stearate | 16; |
| | talc | 9; |
| | ethylcellulose | 1; |
| | purified shellac | 1; |
| I layer | dextromethorphan hydrobromide | 10; |
| | diprophylline | 100; |
| | talc | 10; |
| | light silica | 5; |
| | corn starch | 5; and |
| | polyethylene glycol | 5. |

EXAMPLE 5

192 g of bunazosin hydrochloride, 1.22 kg of a sucrose fatty acid ester, 200 g of a micropowder of ethylcellulose and 200 g of a vegetable oil were mixed together. Then a solution obtained by dissolving 20 g of ethylcellulose and 20. g of purified shellac in 200 ml of ethyl alcohol was added thereto. The obtained mixture was extruded to give particles of 5 mm in diameter. These particles were air-dried at 40° C. for 12 hours and dressed through 16-mesh and 42-mesh sieves. The particles thus obtained were called R particles. 976 g of the R particles were tumbled in a small plate tumbling granulator and a solution obtained by dissolving and dispersing 20 g of ethylcellulose, 20 g of purified shellac, 300 g of calcium stearate and 160 g of talc in 1.6 kg of ethyl alcohol was gradually added thereto to thereby laminate the latter on the former. Then the particles were air-dried at 40° C. for 12 hours. The particles thus obtained and the layer thus laminated thereon were referred to as C particles and C layer, respectively.

1.107 kg of the C particles were tumbled in a small plate tumbling granulator and a solution obtained by dissolving and dispersing 18 g of bunazosin hydrochloride, 22.5 g of talc, 966 g of lactose, 45 g of light silica, 45 g of sodium croscarmellose and 22.5 g of hydroxypropyl cellulose in 3.5 kg of ethyl alcohol was gradually added thereto to thereby laminate the latter on the former. Then the particles were air-dried at 40° C. for 12 hours. The particles thus obtained and the layer thus laminated thereon were referred to as I particles and I layer, respectively.

1.48 kg of the I particles were mixed together with 1 g of calcium stearate and 15 g of light silica and compressed into tablets each weighing 75 mg. Thus tablets containing the multilayer granules of the present invention were produced.

EFFECTS OF THE INVENTION

In order to illustrate the effects of the present invention, the following Experimental Examples will be given.

EXPERIMENTAL EXAMPLE 1

CONTROL TEST

Sample:
The following C and I particles were prepared as control samples in the present invention.

1.4 kg of granule seeds comprising a mixture of white sugar and corn starch (NPS), which were employed as nuclear seeds, were tumbled in a small plate tumbling granulator and a solution obtained by dissolving and dispersing 400 g of phenylpropanolamine hydrochloride, 550 g of talc, 80 g of light silica, 240 g of stearic acid and 30 g of hydroxypropylcellulose in 3 kg of ethyl alcohol was gradually added thereto to thereby laminate the latter on the former. Then the particles were air dried at 50° C. for 12 hours. The particles thus obtained and the layer thus laminated thereon were referred to as R particles and R layer, respectively.

1350 g of the R particles were tumbled in a small fluidized bed apparatus and a solution obtained by dissolving and dispersing 66.5 g of ethylcellulose and 66.5 g of talc in 1.9 kg of ethyl alcohol was sprayed thereon to thereby laminate the latter on the former to give a weight gain of 130 g per 1350 g of the R particles. Then the particles were air-dried at 50° C. for 12 hours. The particles thus obtained and the layer thus laminated thereon were referred to as C particles and C layer, respectively.

1 kg of the C particles were tumbled in a small fluidized bed apparatus and a solution obtained by dissolving and dispersing 32 g of gum arabic and 1.4 g of light silica in 95 g of water was sprayed thereon to thereby laminate the latter on the former. Then the particles were air-dried at 50° C. for 12 hours. The particles thus obtained and the layer thus laminated thereon were referred to as I particles and I layer, respectively.

Method and Result:

Each sample was introduced into a rotatory basket as specified in Dissolution Test of the Japanese Pharmacopoeia, 10th ed., and subjected to the dissolution test with the use of the 1st liquid as specified in the same. The amount of the eluate was determined by the absorbance at 256 nm with the lapse of time and the dissolution ratio (%) was determined therefrom. Table 1 shows the result.

TABLE 1

| Sample | Time (hr) | | | | |
|---|---|---|---|---|---|
| | 0.5 | 1 | 2 | 3 | 5 |
| C particles | 1.5 | 8.8 | 26.0 | 41.6 | 70.1 |
| I particles | 6.3 | 24.4 | 54.7 | 71.5 | 85.6 |

As shown in Table 1, the dissolution pattern of the C particles is different from that of the I particles, though the two patterns were expected to be the same. This fact suggests that the barrier effect of the C layer was lost by laminating that I layer thereon. Thus it was revealed that the release-controlling mechanism of the slow-release phase could not be protected by using a conventional film layer obtained by prior arts.

EXPERIMENTAL EXAMPLE 2

CONTROL TEST

Sample:

C and I particles were prepared in the same manner as the one described in Experimental Example 1 except that the nuclear seeds and each layer had the following composition by weight:

| nuclear seed | NPS | 70; |
|---|---|---|
| R layer | dextromethorphan hydrobromide | 20; |
| | sucrose fatty acid ester | 8; |
| | corn starch | 1; |
| | hydroxypropylcellulose | 1; |
| C layer | ethylcellulose | 3.34; |
| | purified shellac | 3.33; |
| | methylcellulose | 3.33; |
| I layer | gum arabic | 4.8; and |
| | light silica | 0.2. |

Method and Result:

The same dissolution test as the one described in Experimental Example 1 was performed. The amount of the eluate was determined by the absorbance at 275 nm with the lapse of time and the dissolution ratio (%) was determined therefrom. Table 2 shows the result. The same conclusion as the one described in Experimental Example 1 could be drawn from Table 2.

TABLE 2

| Sample | Time (hr) | | | | | |
|---|---|---|---|---|---|---|
| | 0.5 | 1 | 2 | 3 | 5 | 7 |
| C particles | 2.5 | 5.0 | 11.3 | 17.5 | 30.0 | 45.0 |
| I particles | 15.0 | 23.1 | 40.0 | 55.6 | 68.8 | — |

EXPERIMENTAL EXAMPLE

CONTROL TEST

Sample:

$C_1$, $C_2$, $I_1$ and $I_2$ particles were prepared in the following manner.

The $C_1$, $C_2$ and $I_1$ particles were prepared in the same manner as the one described in Experimental Example 1 except that nuclear seeds and each layer had the following compositions by weight:

| nuclear seed: | NPS | 70; |
|---|---|---|
| R layer: | dextromethorphan hydrobromide | 20; |
| | sucrose fatty acid ester | 8; |
| | corn starch | 1; |
| | hydroxypropylstarch | 1; |
| $C_1$ layer: | ethylcellulose | 2.25; |
| | purified shellac | 2.25; |
| | methylcellulose | 2.25; |
| | triacetylglyceride | 0.75; |
| $C_2$ layer: | hydroxypropyl methyl phthalate | 2.25; |
| | microcrystalline wax | 0.75; |
| $I_1$ layer: | gum arabic | 4.8; and |
| | light silica | 0.2. |

Then 1.155 kg of the I1 particles were tumbled in a small plate tumbling granulator and a solution obtained by dissolving and dispersing 100 g of dextromethorphan, 1 kg of diprophylline, 140 g of talc, 140 g of light silica and 40 g of polyethylene glycol in 10 l of ethyl alcohol was gradually added thereto to thereby laminate the latter on the former. Then the particles were air-dried at 50° C. for 12 hours. The particles thus obtained and the layer thus laminated thereon were referred to as $I_2$ particles and $I_2$ layer, respectively.

Method and Result:

The same dissolution test as the one described in Experimental Example 1 was performed. The dissolution ratio (%) of the dextromethorphan in each of the $C_2$, $I_1$ and $I_2$ particles was determined with the lapse of time while that (%) of the diprophylline in the $I_2$ particles was similarly determined. Table 3 shows the result.

TABLE 3

| Sample | Object compound | Time (hr) | | | | |
|---|---|---|---|---|---|---|
| | | 0.5 | 1 | 2 | 3 | 5 |
| $C_2$ particles | dextromethorphan hydrobromide | 1.5 | 4.2 | 9.5 | 15.6 | 30.6 |
| $I_1$ particles | dextromethorphan hydrobromide | 4.2 | 5.8 | 8.3 | 14.4 | 24.4 |

TABLE 3-continued

| Sample | Object compound | Time (hr) | | | | |
|---|---|---|---|---|---|---|
| | | 0.5 | 1 | 2 | 3 | 5 |
| $I_2$ particles | dextromethorphan hydrobromide | 51.9 (18.6) | 61.9 (28.6) | 75.0 (41.7) | 83.1 (50.3) | 92.5 (59.2) |
| | diprophylline | 95.0 | 98.2 | 99.3 | 103.5 | 98.7 |

Since the diprophylline in the $I_2$ layer was rapidly dissolved, it is assumed that the dextromethorphan hydrobromide (33.3%) in the same layer ($I_2$) might be rapidly dissolved similarly. Thus the dissolution of the slow-release moiety in the $I_2$ particles can be expressed by the values in the parentheses which are determined by subtracting the dissolution of said rapid-release moiety. A comparison among the dissolution ratios of the slow-release moieties in the $C_2$, $I_1$ and $I_2$ particles indicates that the dissolution pattern of the $C_2$ particles is similar to that of the $I_1$ particles but significantly different from that of the $I_2$ particles, which suggests that the slow-release characteristic of the $I_2$ particles was significantly damaged. Therefore the following conclusion may be drawn. Namely, strengthening of the C layer by dividing the same into two layers, i.e., $C_1$ and $C_2$, is somewhat effective. Thus it is possible to protect the release-controlling mechanism to such an extent as to allow laminating of the $I_1$ layer thereon. However this effect is yet insufficient so that any protective effect is no longer observed when the $I_2$ layer was further laminated thereon. This result suggests that it is impossible to protect the release-controlling mechanism of the slow-release phase with the use of a conventional film layer obtained by prior arts even if the layer is strengthened by dividing the same into two layers.

EXPERIMENTAL EXAMPLE 4

Sample:

The multilayer granules of the present invention as produced in Example 1 were employed as a test sample. Further multilayer granules, which were produced according to the procedure of Example 1 except that microcrystalline wax was used instead of the calcium stearate, were employed as a control sample.

Method and Result:

Dissolution ratios (%) were determined with the lapse of time in the same manner as the one described in Example 2. Table 4 shows the result.

TABLE 4

| Sample | Time (hr) | | | | | | | | |
|---|---|---|---|---|---|---|---|---|---|
| | 0.5 | 1 | 2 | 3 | 4 | 5 | 6 | 9 | 10.5 |
| Control | 102 | 98 | 100 | 100 | 101 | 97 | 100 | 101 | 98 |
| Test sample | 35 | 45 | 63 | 78 | 90 | 96 | 100 | 99 | 99 |

Table 4 suggests that the multilayer granules obtained by prior arts lost the release-controlling mechanism while that of the multilayer granules of the present invention is maintained owing to the protective effect of the film layer according to the present invention.

EXPERIMENTAL EXAMPLE 5

Sample and Method:

The multilayer granules of the present invention (1), (2) and (3) as produced in Example 2 were employed as samples. Each sample was immersed in the 1st liquid as specified in the Japanese Pharmacopoeia for the first two hours to determine the dissolution ratio. Then it was taken out therefrom and introduced into the 2nd liquid as specified in the same and the dissolution ratio was determined again.

Result:

Table 5 shows the result. The dissolution ratio after two hours was shown by adding thereto the dissolution ratio with the 1st liquid for two hours.

TABLE 5

| Sample | Time (hr) | | | | | | | | |
|---|---|---|---|---|---|---|---|---|---|
| | 0.5 | 1 | 2 | 4 | 5 | 6 | 7 | 8.5 | 10 |
| (1) | 40 | 42 | 42 | 45 | 46 | 47 | 47 | 49 | 51 |
| (2) | 44 | 50 | 52 | 60 | 62 | 65 | 68 | 73 | 78 |
| (3) | 45 | 53 | 64 | 78 | 83 | 87 | 90 | 95 | 100 |

Table 5 suggests that the releasing period would be prolonged with an increase in the content of the magnesium stearate in the film layer according to the present invention and that a preferable content thereof is 80% or below.

EXPERIMENTAL EXAMPLE 6

Sample and Method

The multilayer granules of the present invention (4), (5), (6) and (7) as produced in Example 3 were used as samples. The dissolution ratios were determined in the same manner as the one described in Experimental Example 5.

Result:

Table 6 shows the result. The description with regard to Table 5 is similarly applied thereto.

TABLE 6

| Sample | Time (hr) | | | | | | | | |
|---|---|---|---|---|---|---|---|---|---|
| | 0.5 | 1 | 2 | 3 | 4 | 5 | 6 | 7 | 8.5 | 10 |
| (4) | 15 | 16 | 16 | — | — | 17 | — | — | — | 20 |
| (5) | 20 | 20 | 21 | 25 | 26 | 30 | 35 | 40 | 52 | 62 |
| (6) | 28 | 31 | 39 | 43 | 51 | 66 | 71 | 85 | 90 | 96 |
| (7) | 32 | 35 | 45 | 63 | 85 | 99 | 96 | 98 | 102 | 99 |

Table 6 suggests that a preferable content of the calcium stearate in the film layer according to the present invention is 15 to 70%.

EXPERIMENTAL EXAMPLE 7

Sample and Method:

The multilayer granules of the present invention as produced in Example 4 were employed as a sample and stored at room temperature for a month, at 45° C. for a month and at 55° C. for a month. Then the dissolution ratios were determined in the same manner as the one described in Experimental Example 5.

Result:

Table 7 shows the result. The description with regard to Table 5 is similarly applied thereto.

Table 7 suggests that the film layer according to the present invention would not lose its protective effect on the release-controlling mechanism under various storage conditions.

TABLE 7

| Storage condition | | At room temp. 1 month | At 45° C. 1 month | At 55° C. 1 month |
|---|---|---|---|---|
| Time (hr) | 0.5 | 38 | 37 | 39 |
| | 1 | 45 | 47 | 44 |
| | 2 | 52 | 51 | 48 |
| | 3 | 55 | 53 | 53 |
| | 4 | 60 | 59 | 60 |

TABLE 7-continued

| Storage condition | At room temp. 1 month | At 45° C. 1 month | At 55° C. 1 month |
|---|---|---|---|
| 5 | 68 | 66 | 66 |
| 6 | 72 | 70 | 71 |
| 7 | 78 | 76 | 78 |
| 8.5 | 86 | 86 | 85 |
| 10 | 91 | 89 | 90 |
| 11.5 | 95 | 94 | 95 |
| 13 | 100 | 97 | 99 |

EXPERIMENTAL EXAMPLE 8

Sample and Method:
The R particles and tablets are produced in Example 5 were employed as samples. The R particles and tablets were subjected to the dissolution test by the rotatory basket method and by the paddle method, respectively, to thereby determine the dissolution ratios.
Water was used as the eluent.
Result:

TABLE 8

| Sample | Time (hr) | | | | | | | |
|---|---|---|---|---|---|---|---|---|
| | 1 | 2 | 3 | 4 | 6 | 8 | 10 | 22 |
| R particles | 34 | 37 | 40 | 44 | 50 | 61 | 69 | 98 |
| Tablets | 29 | 33 | 38 | 40 | 48 | 58 | 76 | 94 |

Table 8 suggests that the film layer according to the present invention would not lose its protective effect on the release-controlling mechanism after applying a compression force thereto.

What is claimed is:

1. A multilayer granule for pharmaceutical applications comprising a slow-release layer containing a pharmaceutically-active material adapted to be slowly released when the granule is ingested, a rapid-release layer surrounding said slow-release layer and containing a pharmaceutically-active material adapted to be rapidly released when the granule is ingested, and a first film barrier layer consisting essentially of 10–80 percent by weight of a metal stearate selected from the group consisting of calcium stearate and magnesium stearate and a film-forming component selected from the group consisting of ethyl cellulose, hydroxypropyl methyl cellulose, shellac and wax, said film layer being free of a pharmaceutically-active material and being located between and adjacent to both of said slow-release layer and said rapid-release layer.

2. The multilayer granule of claim 1 wherein a second film layer and a second rapid-release layer are provided on the granule, said second film layer being provided on said rapid-release layer and said second rapid-release layer being provided on said second film layer and adapted to release a pharmaceutically active material faster than said rapid-release layer.

3. The multilayer granule of claim 1 wherein said multilayer granule is enclosed in a hard capsule.

4. The multilayer granule of claim 1 wherein said multilayer granule is formulated into a compressed tablet.

5. The multilayer granule of claim 1 in which said film layer contains 15 to 70% of said metal stearate.

6. A multilayer granule for pharmaceutical applications comprising a slow-release core containing a pharmaceutically-active material adapted to be slowly released when the granule is ingested, a rapid-release layer surrounding said core and containing a pharmaceutically-active material adapted to be rapidly released when the granule is ingested, and a film barrier layer consisting essentially of 10–80 percent by weight of a metal stearate selected from the group consisting of calcium stearate and magnesium stearate and a film-forming component selected from the group consisting of ethyl cellulose, hydroxypropyl methyl cellulose, shellac and wax, said film barrier layer being free of a pharmaceutically-active material and being located between and adjacent to both the core and the rapid-release layer.

7. The multilayer granule of claim 6 in which said film layer contains 15 to 70% of said metal stearate.

8. A multilayer granule for pharmaceutical applications comprising a slow release layer containing a pharmaceutically-active material adapted to be slowly released when the granule is ingested, a rapid-release layer surrounding said slow-release layer and containing a pharmaceutically-active material adapted to be rapidly released when the granule is ingested, and a film barrier layer consisting essentially of 10–80 percent by weight of a metal stearate selected from the group consisting of calcium stearate and magnesium stearate and a film-forming component selected form the group consisting of ethyl cellulose, hydroxypropyl methyl cellulose, shellac and wax, said film layer being free of a pharmaceutically-active material and being located between and adjacent to both of said slow-release layer and said rapid-release layer.

9. A multilayer granule for pharmaceutical applications comprising a slow release core containing a pharmaceutically-active material adapted to be slowly released when the granule is ingested, a rapid-release layer surrounding said core and containing a pharmaceutically-active material adapted to be rapidly released when the granule is ingested, and a film barrier layer consisting essentially of 10–80 percent by weight of a metal stearate selected from the group consisting of calcium stearate and magnesium stearate and a film-forming component selected from the group consisting of ethyl cellulose, hydroxy propyl methyl cellulose, shellac and wax, said film barrier layer being free of a pharmaceutically-active material and being located between and adjacent to both the core and the rapid-release layer.

10. A multilayer granule for pharmaceutical applications comprising a slow-release layer containing a pharmaceutically active material adapted to be slowly released when the granule is ingested, a rapid-release layer surrounding said slow-release layer and containing a pharmaceutically active material adapted to be rapidly released when the granule in ingested, and a film barrier layer consisting essentially of 18.5–90.9 percent by weight of a metal stearate selected from the group consisting of calcium stearate and magnesium stearate and a film-forming component selected from the group consisting of ethyl cellulose, hydroxypropyl methyl cellulose, shellac and wax, said film layer being free of a pharmaceutically active material and being located between and adjacent to both of said slow-release layer and said rapid-release layer.

11. A multilayer granule for pharmaceutical applications comprising a slow-release layer containing a pharmaceutically-active material adapted to be slowly released when the granule is ingested, a rapid-release layer surrounding said slow release layer and containing a pharmaceutically-active material adapted to be rapidly released when the granule is ingested, and a film barrier layer consisting essentially of 10-80 percent by weight of a metal stearate selected from the group consisting of calcium stearate and magnesium stearate, a film-forming component selected from the group consisting of methyl cellulose, ethyl cellulose, hydroxypropyl methyl cellulose, shellac and one or more additives selected from the group consisting of vinyl acetate and talc, said film layer being free of pharmaceutically-active material and being located between and adjacent to both of said slow-release layer and said rapid-release layer.

12. The multilayer granule of claim 11 wherein said film barrier layer consists essentially of ethyl cellulose, purified shellac, calcium stearate and talc.

13. The multilayer granule of claim 11 wherein said film barrier layer consists essentially of magnesium stearate, polymeric vinyl acetate and methyl cellulose.

* * * * *